US00PP15992P3

(12) United States Plant Patent
Smaal

(10) Patent No.: US PP15,992 P3
(45) Date of Patent: Sep. 27, 2005

(54) *KALANCHOE* PLANT NAMED 'PIPPIJN'

(50) Latin Name: *Kalanchoe blossfeldiana*
Varietal Denomination: Pippijn

(75) Inventor: Andres Smaal, De Kwakel (NL)

(73) Assignee: A.B. Breeding BV, Kwakel (NL)

( * ) Notice: Subject to any disclaimer, the term of this patent is extended or adjusted under 35 U.S.C. 154(b) by 121 days.

(21) Appl. No.: 10/644,660

(22) Filed: Aug. 20, 2003

(65) Prior Publication Data

US 2004/0034897 P1 Feb. 19, 2004

Related U.S. Application Data

(63) Continuation of application No. 10/024,685, filed on Dec. 14, 2001, now abandoned.

(51) Int. Cl.[7] ..... A01H 5/00
(52) U.S. Cl. ..... Plt./341
(58) Field of Search ..... Plt./341

(56) References Cited

PUBLICATIONS

Netherlands PBR Publication Document relating to Application KLN 276 (1 page)—in Dutch.

*Primary Examiner*—Bruce R. Campell
*Assistant Examiner*—S B McCormick-Ewoldt
(74) *Attorney, Agent, or Firm*—Wood, Phillips, Katz, Clark & Mortimer

(57) ABSTRACT

A new and distinct cultivar of *Kalanchoe* plant named Pippijn is provided. This new cultivar is characterized by its bright red flowers, dark green foliage, compact growth habit and excellent basal branching.

1 Drawing Sheet

Latin name of genus and species of plant claimed: *Kalanchoe blossfeldiana.*
Variety denomination: 'Pippijn'.

BACKGROUND OF THE INVENTION

The present invention comprises a new and distinct *Kalanchoe* plant, botanically known as *Kalanchoe blossfeldiana*, and hereinafter referred to by the cultivar name 'Pippijn'.

The new cultivar was developed by the inventor through a controlled breeding program during August 1995 in The Netherlands. The female (seed) parent of 'Pippijn' was the proprietary *Kalanchoe blossfeldiana* selection designated '93114-057' (not patented) characterized by its red flowers. The male (pollen) parent of 'Pippijn' was the propriety *Kalanchoe* selection designated '94077' (not patented), characterized by its purple flowers and dark green foliage. 'Pippijn' was discovered and selected as a flowering plant within the progeny of the stated cross by the inventor in June 1996.

Asexual reproduction of the new cultivar at Arroyo Grande, Calif. and West Chicago, Ill. has been through the use of terminal vegetative cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits bright red flowers, (b) forms dark green foliage, (c) exhibits a good basal branching character, and (d) exhibits a compact upright growth habit.

The new cultivar of the present invention can be compared to 'Calbuco' (patent status unknown). In side by side comparisons with 'Calbuco', it is found that the new cultivar is less compact, more floriferous and exhibits smaller flowers of a darker red color. A detailed comparison can be found in Table 1.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown in a greenhouse at West Chicago, Ill., U.S.A.

DETAILED BOTANICAL DESCRIPTION

The cultivar Pippijn has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Jan. 4, 2001 between 9:00 and 9:30 am under natural daylight. The plants used for the following observations and measurements were produced from cuttings taken from stock plants and grown in West Chicago, Ill. in 10 cm pots for sixteen (16) weeks. Plants were grown in a double poly carbonate covered greenhouse under conditions comparable to those used in commercial practice while utilizing a soilless growth medium and maintaining temperatures of approximately 82° F. during the day and approximately 66° F. during the night. Plants were exposed to three weeks of long days followed by 9 weeks of short days. Growth regulators were applied as follows: B nine, 3000 ppm at days 17 and 28 and 1500 ppm day 42.

Classification:

*Botanical.*—*Kalanchoe blossfeldiana*, cultivar 'Pippijn'.

Parantage:

*Male* (*pollen*) *parent.*—Proprietary *Kalanchoe blossfeldiana* selection #'94077'.

*Female* (*seed*) *parent.*—Proprietary *Kalanchoe blossfeldiana* selection #'93114-057'.

Propagation:

*Type cutting.*—Terminal tip.

*Time to initiate roots.*—Approximately 7–14 days with the shorter times generally being experienced in the summer and the longer times in the winter. Time to develop roots — Approximately 21 days.

*Root description.*—Fibrous, branching.

Plant description:

*Habit of growth.*—Moderately vigorous with good basal branching. A mature plant, at 16 weeks after the planting of an unrooted cutting, commonly measures approximately 13.1 cm in height and approximately 11.9 cm in width.

*Branching habit.*—Typically forms one main stem 11 cm in length and 5 mm in diameter and 11 lateral branches approximately 6 cm in length and 3 mm in diameter. Internode length: approximately 1.2 cm.

*Plant form.*—Upright and mounded.

*Foliage.*—Form: Simple. Arrangement: Opposite. Shape: Ovate with obtuse apex, cuneate base and crenate margin. Texture: Glabrous, succulent. Size of mature foliage: Approximately 6.7 cm in length and approximately 4.9 cm in width. Color of mature foliage: Upper surface closest to 137A and 139A; lower surface closest to 137B. Petiole length: Approximately 1.3 cm. Petiole diameter: Approximately 3.2 mm. Petiole color: Closest to 137k.

Flower description:

*Flowering habit.*—Freely flowering.

*Natural flowering season.*—Early January. Flowering time is dependent on temperature, light intensity and other growing conditions.

*Flowering response time.*—Approximately 11 weeks.

*Inflorescence type.*—Dichasial cymes.

*Flowers borne.*—Above foliage.

*Flower longevity.*—Approximately 7 days.

*Fragrance.*—None.

*Quantity of flowers.*—Approximately 24 flowers on main stem and 15 flowers on each lateral branch.

*Flower buds.*—Shape: Elliptical, becoming elongated as it matures. Size just before opening: Length is approximately 1.1 cm, width is approximately 5 mm. Color is 43D.

*Flower.*—Salverform. Corolla: Diameter is approximately 1 cm, depth is approximately 3 mm and aspect is cupped. Corolla tube length is approximately 9.5 mm and diameter is approximately 3 mm.

*Petals.*—Number: Four. Shape: Ovate with cuspidate apex, rounded base. Approximate size: 7 mm in length, 6 mm in width. Aspect: Slightly convex. Texture: Glabrous. Appearance: Somewhat iridescent.

*Mature flower color.*—Upper surface of petals is closest to 53B fading to slightly more blue than 53B at senescence; lower surface of petals is closest to 43D.

*Sepals.*—Number: Four. Shape: Lanceolate with acute apex, entire margin. Size: 6 mm in length, 2 mm in width. Texture: Glabrous. Color: Upper and lower surface: 144B.

*Peduncle.*—Length: Approximately 0.9 cm in length and 2 mm in diameter.

*Pedicel length.*—Approximately 5 mm.

*Reproductive organs.*—Androecium: 8 stamens arranged in two groups of four — one group being shorter than the other. Anther shape is oblong and flat; length is <1 mm. Pollen color is 6C. Gynoecium: Stigma shape is flat, appearance is crystalline, colorless and transparent, size is <1 mm in length. Style length is approximately 2 mm; color is 151D. Ovary is: 4 celled, 6.5 mm in length. Color is 144B.

Seed development: Seed development has not been observed.

Disease resistance: Resistance to known *Kalanchoe* pathogens has not been observed.

TABLE 1

| CHARACTERISTIC | 'PIPPIJN' | 'CALBUCO' |
|---|---|---|
| PLANT HEIGHT | 13.1 cm | 9.5 cm |
| NUMBER OF BRANCHES | 11 | 13 |
| FLOWER DIAMETER | 1 cm | 1.8 cm |
| PETAL COLOR-FULLY OPENED-UPPER SURFACE | 53B | Between 54A and 51A |
| APPROXIMATE NUMBER OF FLOWERS PER PLANT | 186 | 50 |
| COROLLA DIAMETER | .9 cm | 1.8 cm |

I claim:

1. A new and distinct cultivar of *Kalanchoe* plant named 'Pippijn' substantially as herein shown and described, which:

(a) exhibits dark red flowers, (b) forms dark green foliage, (c) exhibits a good basal branching character, and (d) exhibits a compact upright growth habit.

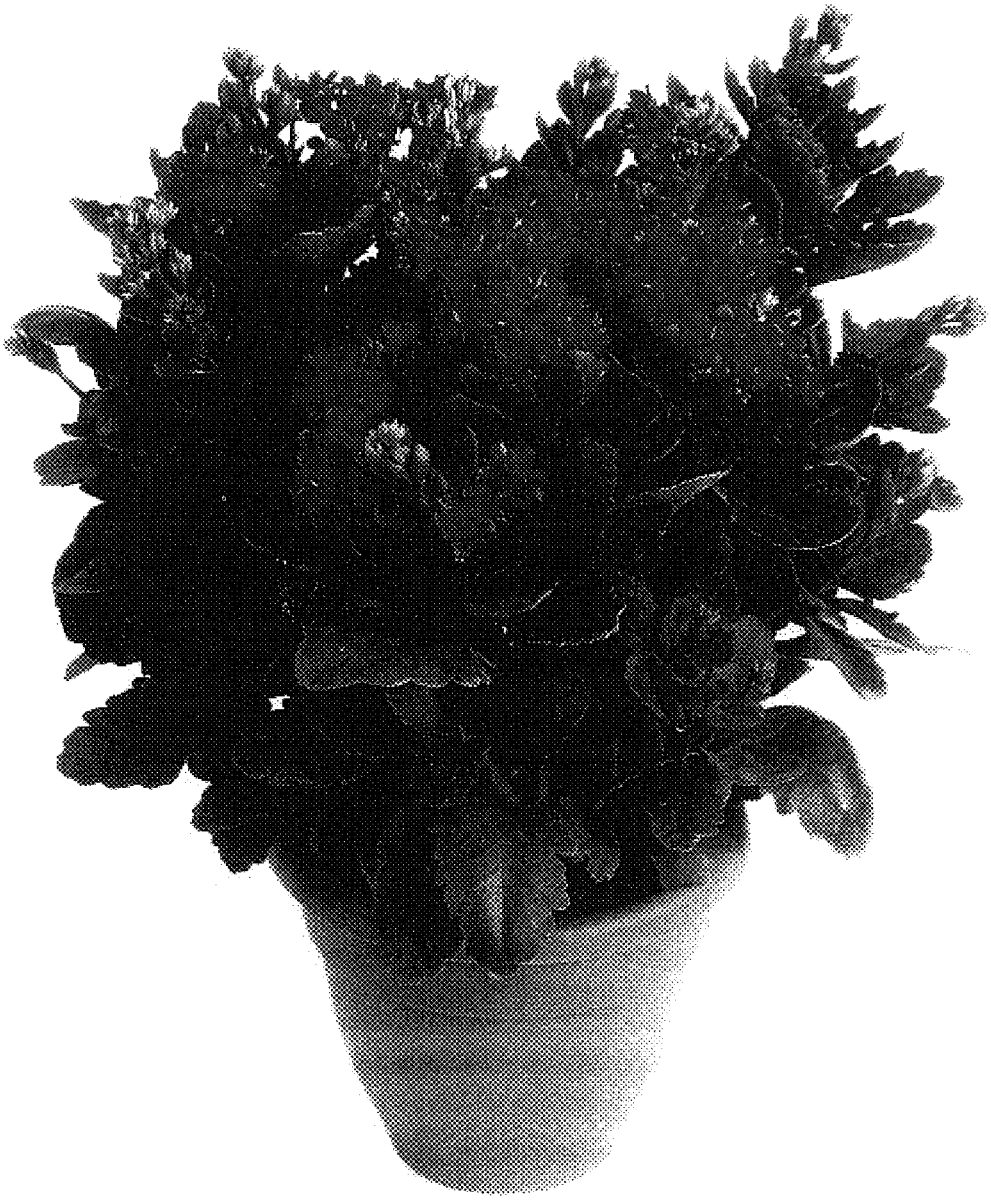

* * * * *